US00PP34461P3

(12) United States Plant Patent
Olesen

(10) Patent No.: US PP34,461 P3
(45) Date of Patent: Aug. 2, 2022

(54) MINIATURE ROSE PLANT NAMED 'POULPAR116'

(50) Latin Name: *Rosa hybrida*
Varietal Denomination: 'Poulpar116'

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,615

(22) Filed: Sep. 7, 2021

(65) Prior Publication Data

US 2022/0095504 P1 Mar. 24, 2022

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./116, 118
See application file for complete search history.

(56) References Cited

PUBLICATIONS

UPOV Pluto 2022.*

* cited by examiner

*Primary Examiner* — Annette H Para

(57) ABSTRACT

A new garden rose plant of the Miniature class which has abundant, apricot yellow blend flowers and attractive foliage. This new and distinct variety has shown to be uniform and stable in the resulting generations from asexual propagation.

1 Drawing Sheet

Botanical designation: *Rosa hybrida.*

Variety denomination: 'Poulpar116'.

This application claims priority to Plant Breeder's Rights Application Number 2020/2262, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpar116', originated as a single seedling from the stated cross.

The new variety may be distinguished from its male pollen parent and female seed parent primarily by the following characteristics. The male pollen parent plant has deep yellow flowers while the new variety has apricot yellow blend flowers. The female seed parent plant has pink flowers while the new variety has apricot yellow blend flowers.

The objective of the hybridization of this rose variety was to create a new and distinct variety with unique qualities, such as:

1. Uniform and abundant apricot yellow blend flowers;
2. Vigorous, but compact growth when propagated on its own roots;
3. Exceptional disease resistance.

This combination of qualities is not present in previously available commercial cultivars of this type, known to the inventor, and distinguish 'Poulpar116' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpar116' was selected in the spring of 2013 by the inventor as a single plant from the progeny of the aforementioned hybridization.

Asexual reproduction of 'Poulpar116' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpar116' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar116'. Specifically illustrated in the drawing are open flowers viewed from above and the side, flower buds at various stages of development, leaves, bare stems, flower petals detached showing reproductive flower parts. Plants shown are four months of age.

DETAILED DESCRIPTION OF THE VARIETY

The following is a description of 'Poulpar116', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulpah091', U.S. Plant Pat. No. 30,350 are compared to 'Poulpar116' in Chart 1.

CHART 1

| | 'Poulpar116' | 'Poulpah091' |
|---|---|---|
| Petal Count | 80 | 55 |
| Flower Diameter | 60 mm | 80 mm |
| General Tonality of Flower Color | Orange Group 24C and Yellow-Orange Group 23B | Yellow-Orange Group 19B and Orange Group 24C |

Flower and flower bud:

*Blooming habit.*—Continuous.

*Flower bud.*—Size: Upon opening, 26 mm in length from base of receptacle to end of bud. Bud diameter is 17 mm. Bud form: Ovoid with a flattened base. Bud color: As sepals divide petals are Greyed-Red Group 180C. Sepal inner surface: Color: Yellow-Green Group 146D. Surface: Lightly pubescent. Sepal outer surface: Color: Yellow-Green Group 144A. Texture: Smooth. Sepal Shape: Apex: Cirrhose. Base: Flat at union with receptacle. Sepal Margin: Margins have strong foliaceous appendages on three of the five sepals. Sepal size: About 22 mm long, 10 mm wide. Receptacle: Texture: Smooth. Size: 6 to 9 mm in height, 6 mm wide. Color: Yellow-Green Group 144A. Shape: Funnel. Pedicel: Surface: Smooth. Length: 50 mm. Diameter: 3 to 4 mm. Color: Yellow-Green Group 144A. Strength: Strong.

*Flower bud development.*—Flower buds are borne singly.

*Flower bloom.*—Fragrance: Moderate. Duration: The blooms have a duration on the plant of approximately 20 days. Petals fall cleanly away from plant after flowers have fully matured. Size: Flower diameter is 60 mm when open. Flower depth is 26 mm. Flower shape: Rosette. Shape of flower, side view: The upper portion is convex. The lower portion is deeply concave.

*Petalage.*—Under normal conditions, flowers have about 80 petals.

*General tonality of flower.*—Open flowers are Orange Group 24C and Yellow-Orange Group 23B.

*Petal color.*—Outer petals. Upper surface: Yellow-Orange Group 16B with Orange Group 25C streaks. Lower surface: Orange-Red Group 31B with streaks of Yellow Group 13B. Inner petals: Upper surface: Yellow-Orange Group 16B with Yellow Group 6B streaks. Lower surface: Orange Group 24B with streaks of Yellow Group 8B. Basal petal spots: Upper surface: Yellow Group 6B. Lower surface: Yellow Group 6C.

*Petals.*—Petal Reflex: Strong bilateral. Margin: Entire and uniform. Moderate undulations. Shape: Broad and elliptic. Apex shape: Rounded. Base shape: Acute. Size: 20 mm (l)×9 mm (w). Texture: Smooth. Thickness: Average.

*Petaloids.*—Size: 12 mm (l) by 9 mm (w). Quantity: About 10. Shape: Elliptical with an acute base and rounded or acute apex. Color: The upper surface of petaloids is Yellow-Orange Group 16B streaked with Yellow Group 6B from the basal zone to the middle zone. The Lower surface is Orange Group 24B with streaks of Yellow Group 8B. Lower surface basal petaloid spot is Yellow Group 6C.

*Reproductive flower parts.*—Pollen: None observed. Anthers: Size: 1.5 mm in length. Color: Greyed-Yellow Group 160C. Quantity: 30 on average. Filaments: Color: Yellow Group 12A. Length: 3 mm. Pistils: Length: 12 mm. Quantity: 20 on average. Stigmas: Color: Greyed-Yellow Group 160A. Styles: Color: Green-White Group 157A with intonations of Red-Purple Group 58B. Location of stigmas: Superior in location relative to the length of the filaments and the height of the anthers. Hips: None Observed.

Plant:

*Plant growth.*—Upright compact. Plants are about 40 cm in height and 35 cm wide.

*Stems.*—Color of juvenile growth: Yellow-Green Group 144B. Color of mature growth: Yellow-Green Group 144A. Length: Canes are about 20 cm from the base of the plant to the flowering portion. Diameter: About 3 mm. Internodes: On mature canes about 35 mm between nodes. Surface Texture: Young wood: Smooth. Older wood: Smooth.

*Long prickles.*—Incidence: About 2 prickles per 10 cm of stem. Size: Average length of prickles on mature stems is 8 mm. Shape: Upper portion is linear. Lower portion is linear. Color: Juvenile prickles: Greyed-Red Group 180C. Mature prickles: Greyed-Red Group 180C.

*Plant foliage.*—Compound leaf: 120 mm (l)×93 (w). Quantity: 3 leaves per 10 cm of stem on average. Leaf bearing angle to the stem: 45 degrees. Color of juvenile foliage: Upper side: Yellow-Green Group 144A. Lower side: Yellow-Green Group 144B. Color of mature foliage: Upper side: Yellow-Green Group 147A. Lower side: Yellow-Green Group 146B.

*Plant leaves and leaflets.*—Stipules: Size: 11 mm long, mm wide. Quantity: 2 per compound leaf. Shape: Linear, slightly broad based with outward extending apices. Margins: Finely serrated. Color: Yellow-Green Group 144A. Petiole: Length: About 26 mm. Diameter: 2 mm. Upper surface color: Yellow-Green Group 144A with intonations of Greyed-Red Group 178B. Lower surface color: Yellow-Green Group 144A. Rachis: Length: About 30 mm. Upper surface color: Yellow-Green Group 144A with intonations of Greyed-Red Group 178B. Lower surface color: Yellow-Green Group 144A. Leaflet: Quantity: 5 or 7 leaflets. Margins: Serrated. Size: Terminal leaflets are about 55 mm long, 31 mm wide. Shape: Generally elliptical. Base: Rounded. Apex: Mucronate. Texture: Smooth. Thickness: Average. Arrangement: Odd pinnate. Venation: Reticulate. Glossiness: Not glossy.

*Disease resistance.*—Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

*Cold hardiness.*—The variety is tolerant to USDA Cold Hardiness Zone 6.

*Heat tolerance.*—The variety has been found to be suitable for climate conditions found in the American Horticulture Society heat zone 7.

I claim:

1. A new and distinct variety of rose plant of the Miniature rose class named 'Poulpar116', substantially as illustrated and described herein, due to its abundant apricot yellow blend flowers, disease resistance, and extended period of bloom.

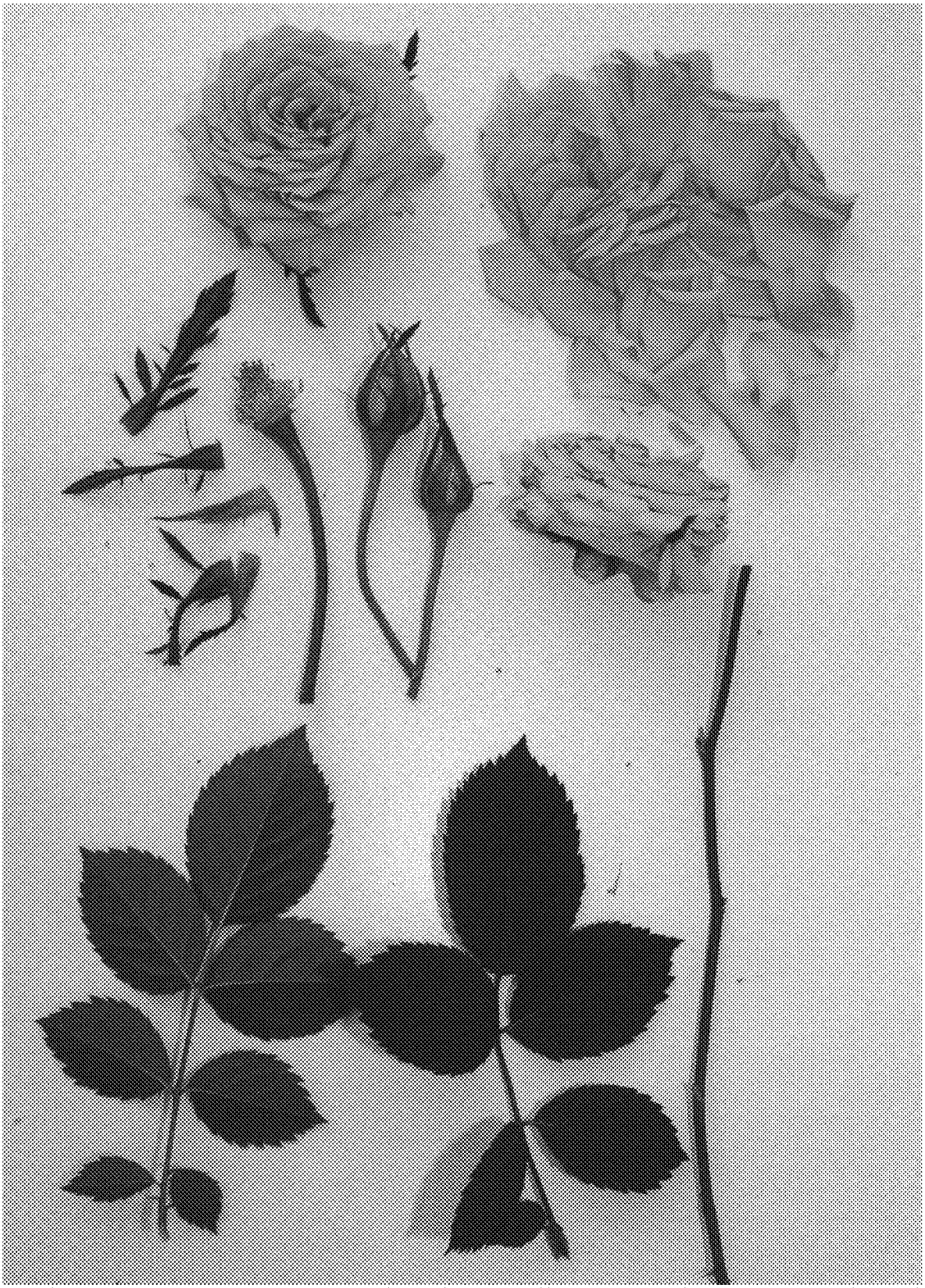

* * * * *